United States Patent
Forsbäck et al.

(10) Patent No.: US 9,925,155 B2
(45) Date of Patent: Mar. 27, 2018

(54) DIALYSIS COMPOSITION

(71) Applicant: Gambro Lundia AB, Lund (SE)

(72) Inventors: Gunita Forsbäck, Löddeköpinge (SE); Viktoria Hancock, Eslöv (SE); Anders Wieslander, Lund (SE); Torbjörn Linden, Haslö (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 14/651,370

(22) PCT Filed: Dec. 18, 2013

(86) PCT No.: PCT/EP2013/077019
§ 371 (c)(1),
(2) Date: Jun. 11, 2015

(87) PCT Pub. No.: WO2014/095953
PCT Pub. Date: Jun. 26, 2014

(65) Prior Publication Data
US 2015/0313858 A1 Nov. 5, 2015

Related U.S. Application Data

(60) Provisional application No. 61/738,572, filed on Dec. 18, 2012.

(30) Foreign Application Priority Data

Dec. 18, 2012 (SE) ........................... 1251447

(51) Int. Cl.
| | | |
|---|---|---|
| A61K 31/194 | (2006.01) | |
| A61K 33/00 | (2006.01) | |
| A61M 1/28 | (2006.01) | |
| A61M 1/16 | (2006.01) | |
| A61K 9/08 | (2006.01) | |
| A61K 45/06 | (2006.01) | |
| A61K 31/7004 | (2006.01) | |
| A61K 33/06 | (2006.01) | |
| A61K 33/14 | (2006.01) | |

(52) U.S. Cl.
CPC ............ *A61K 31/194* (2013.01); *A61K 9/08* (2013.01); *A61K 31/7004* (2013.01); *A61K 33/00* (2013.01); *A61K 33/06* (2013.01); *A61K 33/14* (2013.01); *A61K 45/06* (2013.01); *A61M 1/1654* (2013.01); *A61M 1/287* (2013.01)

(58) Field of Classification Search
CPC .......... A61K 45/06; A61K 33/00; A61K 9/08; A61M 1/287
See application file for complete search history.

(56) References Cited

U.S. PATENT DOCUMENTS

| | | | |
|---|---|---|---|
| 3,560,380 A | 2/1971 | Stade | |
| 4,636,412 A | 1/1987 | Field | |
| 4,756,838 A | 7/1988 | Veltman | |
| 6,610,206 B1 | 8/2003 | Callan et al. | |
| 9,029,333 B2 | 5/2015 | Sugiyama et al. | |
| 2004/0019313 A1 | 1/2004 | Childers et al. | |
| 2004/0057885 A1 | 3/2004 | Taylor | |
| 2004/0060865 A1 | 4/2004 | Callan et al. | |
| 2007/0087212 A1 | 4/2007 | Iyengar et al. | |
| 2007/0231395 A1 | 10/2007 | Kai et al. | |
| 2008/0015487 A1* | 1/2008 | Szamosfalvi ....... A61M 1/3672 604/6.07 |
| 2009/0306002 A1* | 12/2009 | Nakanishi ........... A61K 31/194 514/25 |
| 2010/0120702 A1 | 5/2010 | Sugiyama et al. | |
| 2011/0172583 A1* | 7/2011 | Callan .................. A61K 31/19 604/5.04 |
| 2012/0291875 A1 | 11/2012 | Shah et al. | |

FOREIGN PATENT DOCUMENTS

| | | |
|---|---|---|
| CN | 1938058 A1 | 3/2007 |
| EP | 0 034 916 A1 | 9/1981 |
| EP | 0 399 918 A2 | 11/1990 |
| EP | 0 417 478 A1 | 3/1991 |
| EP | 0 602 014 A1 | 6/1994 |
| EP | 0 602 921 A1 | 6/1994 |
| EP | 1 059 083 A1 | 12/2000 |
| EP | 1 101 483 A2 | 5/2001 |
| EP | 1 192 961 A2 | 4/2002 |
| EP | 1 714 657 A1 | 10/2006 |
| EP | 1 731 183 A1 | 12/2006 |
| EP | 1834652 | 9/2007 |
| EP | 2119438 | 11/2009 |

(Continued)

OTHER PUBLICATIONS

Author: Ledebo, title:On-line Preparation of Solutions for Dialysis: Practical Aspects Versus Safety and Regulations; JASN; vol. 13 No. suppl 1 S78-S83; Jan. 1, 2002.*
Ahmad et al., "Dialysate Made From Dry Chemicals Using Citric Acid Increases Dialysis Dose," American Journal of Kidney Diseases, vol. 35, No. 3 (Mar. 2000): pp. 493-499.
Gabutti et al., "Citrate- vs. acetate-based dialysate in bicarbonate haemodialysis: consequences on haemodynamics, coagulation, acid-base status, and electrolytes," BMC Nephrology 2009, 10:7.
Nilsson, "Citrate vs. Acetate in Bicarbonate-Based Dialysis Fluid—What Does it Mean Clinically?" Gambro Lundia AB, 2012.
Gambro Lundia AB's Response to Opposition filed in related European patent application No. 11729087.4 dated Aug. 5, 2016.

(Continued)

*Primary Examiner* — Yanzhi Zhang
(74) *Attorney, Agent, or Firm* — K&L Gates LLP

(57) ABSTRACT

The present invention relates to an acid concentrate dialysis composition comprising a mixture of citric acid and citrate, having pH of less than 3.0, wherein the total concentration of citrate is between 35 mM and 450 mM, and wherein the amount of citric acid is more than 50% of the total concentration of citrate. The acid concentrate dialysis composition is to be combined to form a dialysis solution having a total concentration of citrate of between 1 and 6 mM.

11 Claims, No Drawings

(56) References Cited

FOREIGN PATENT DOCUMENTS

| | | |
|---|---|---|
| EP | 2123270 | 11/2009 |
| EP | 2 151 247 A1 | 2/2010 |
| EP | 2 286 820 A1 | 2/2011 |
| FR | 2766797 A1 | 2/1999 |
| JP | H04-257522 A | 9/1992 |
| JP | H10-87478 A | 4/1998 |
| JP | 2003104869 | 4/2003 |
| JP | 2005-206572 A | 8/2005 |
| RU | 2006103497 A | 8/2007 |
| TW | 200911287 A | 3/2009 |
| WO | 92/11046 A1 | 7/1992 |
| WO | 00/57935 A1 | 10/2000 |
| WO | 01/21233 | 3/2001 |
| WO | 03/043680 A1 | 5/2003 |
| WO | 2005/002599 A1 | 1/2005 |
| WO | 2010/055963 | 5/2010 |
| WO | 2010/112547 A1 | 10/2010 |
| WO | 2010/112570 | 10/2010 |
| WO | 2011/161055 A1 | 12/2011 |
| WO | 2011/161056 A2 | 12/2011 |
| WO | 2012/175353 A1 | 12/2012 |
| WO | 2012/175354 A1 | 12/2012 |
| WO | 2013/004362 A1 | 1/2013 |

OTHER PUBLICATIONS

Kipouros et al., "A Thermal Analysis of the Production of Anhydrous MgCl2," Journal of Light Metals, May 2001 (Response to Opposition filed in related European patent application No. 11729087.4 on Aug. 5, 2016).

Declaration of David Karlsson relating to film thickness, dated Jul. 29, 2016 (Response to Opposition filed in related European patent application No. 11729087.4 on Aug. 5, 2016).

Annex A (curriculum vitae) of David Karlsson Declaration (Response to Opposition filed in related European patent application No. 11729087.4 on Aug. 5, 2016).

Translation Declaration signed by Don Sanderson on Jul. 22, 2016 attesting to the translation of selected paragraphs of JP 10-87478 (opponent Fresenius Medical Care), (Response to Opposition filed in related European patent application No. 11729087.4 on Aug. 5, 2016).

Experimental annex providing stability data (Response to Opposition filed in related European patent application No. 11729087.4 on Aug. 5, 2016).

Gärtner, Heinz, "Developments in barrier films," Symposium "Sperrschichtfolien [Barrier films]" on Jun. 30/Jul. 1, 2004, Würzburg, Germany.

TW200911287—Translation of Office Action—8 pages.

Ing T.S. et al., Employing L-lactic acid powder in the preparation of a dry "acid concentrate" for use in a bicarbonate-based dialysis solution-generating system: experience in hemodialysis patients, The International journal of artificial organs 1994, vol. 17, nr 2, p. 70-73.

Japanese Office Action for Japanese Application No. 2013-515839, dated Jul. 28, 2015.

Barry et al. (Basis for Using Moisture Vapor Transmission Rate Per Unit Product in the Evaluation of Moisture-Barrier Equivalence of Primary Packages for Solid Oral Dosage Forms, 2004).

CurTec article (http://www.pharmaceutical-networking.com/moisture-resistant-packaging/) 2015.

Nikhil Mehrotra (Masters Theses): A Study of Water Vapor Transmission Rate of Blister Packs by USP Standard and Continuous Gravimetric Protocol 2010.

International Search Report PCT/EP2012/060969 dated Oct. 2, 2012.

Sigma-Aldrich Product Spedification form for Calcium Chloride; downloaded Mar. 15, 2016.

Norner AS download showing WVTR calculation for: FEP layer (1-mm); downloaded Feb. 13, 2015.

Norner AS download showing WVTR calculation for: PMMA layer (1-mm); downloaded Feb. 14, 2015.

Norner AS download showing WVTR calculation for: PTFE layer (1-mm); downloaded Feb. 14, 2015.

Norner AS download showing WVTR calculation for: PTFE-PTFE dual-layer (1-mm); downloaded Feb. 14, 2015.

Norner AS download showing WVTR calculation for: PTFE layer (2-mm); downloaded Feb. 14, 2015.

Norner AS download showing WVTR calculation for: PVDC layer (1-mm); downloaded Feb. 13, 2015.

Norner AS download showing WVTR calculation for: PTFE-PMMA dual-layer (1-mm); downloaded Feb. 14, 2015.

Oracle Packaging; data for aluminum foil; downloaded Feb. 16, 2015.

International Search Report PCT/EP2012/060971 dated Aug. 21, 2012.

Magnesium chloride 4.5 hydrate, European Pharmacopoeia 7.3 Jan. 2012.

International Preliminary Report on Patentability for International Application No. PCT/EP2012/075008, dated Jun. 24, 2014.

International Search Report for International Application No. PCT/EP2012/075008, dated Mar. 6, 2013.

Written Opinion of the International Searching Authority for International Application No. PCT/EP2012/075008, dated Mar. 6, 2013.

International Preliminary Report on Patentability for International Application No. PCT/EP2012/075007, dated Jun. 24, 2014.

International Search Report for International Application No. PCT/EP2012/075007, dated Mar. 6, 2013.

Written Opinion of the International Searching Authority for International Application No. PCT/EP2012/075007, dated Mar. 6, 2013.

Search Report for related International Patent Application No. PCT/EP2013/054386 dated May 23, 2013 (6 pages).

Written Opinion for related International Patent Application No. PCT/EP2013/054386 dated May 23, 2013 (5 pages).

English translation of Japanese Office Action dated Nov. 22, 2016 in corresponding Japanese application No. 2014-560335 (4 pages).

Notice of Opposition filed in related European Patent case No. 11729087.4-1453 / 2585076 by Fresenius Medical Care AG & Co. KGaA on Dec. 3, 2015 (16 pages).

Vortrag Dr. Gärtner mit dem Titel, "Entwicklungen bei Sperrschichtfolien", ("Fachtagung, Sperrschichtfolien" vom 30. Juni/1 Juli 2004 in Wurzburg) nebst eidesstattlicher Versicherung des Hernn Dietmar Hansel (Notice of Opposition filed in related European patent application No. case No. 11729087.4-1453 / 2585076 by Fresenius Medical Care AG & Co. KGaA on Dec. 3, 2015) (35 pages).

Summons to attend oral proceedings pursuant to Rule 115(1) EPC issued in related European Patent case No. 11729087.4-1453 / 2585076 on Aug. 30, 2016 (9 pages).

Observations (Experimental Data) filed in related European patent application No. case No. 11729087.4-1453 / 2585076 by Gambro Lundia AB on Aug. 5, 2016 (5 pages).

Declaration of Ola Carlsson filed in related European patent application No. case No. 11729087.4-1453 / 2585076 by Gambro Lundia AB on Aug. 5, 2016 (13 pages).

\* cited by examiner

DIALYSIS COMPOSITION

PRIORITY CLAIM

This application is a 371 National Stage Application of International Application No. PCT/EP2013/077019, filed Dec. 18, 2013, which claims priority to and the benefit of U.S. Application Ser. No. 61/738,572, filed on Dec. 12, 2012 and Swedish Application No. 1251447-7, filed Dec. 12, 2012, the disclosures of each of which are incorporated by reference herein in their entireties.

TECHNICAL FIELD

The present invention concerns dialysis compositions, and more specifically dialysis compositions comprising citric acid and citrate.

BACKGROUND

Dialysis is a well established treatment technique for patients having kidney malfunction. The dialysis treatment artificially replaces the functions of the kidney. There are two distinct types of dialysis; hemodialysis and peritoneal dialysis.

Hemodialysis involves withdrawing blood from the body and cleaning it in an extracorporeal blood circuit, and then returning the cleansed blood to the body. The extracorporeal blood circuit includes a dialyzer which comprises a semipermeable membrane. The semipermeable membrane has a blood side and a dialysate side, and waste substances and excess fluid are removed from the blood passing on the blood side of the semipermeable membrane through the semipermeable membrane over to the dialysate side of the semipermeable membrane.

Hemodialysis may be performed in three different treatment modes, hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis fluid is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis fluid, through the semipermeable membrane and into the blood.

In hemofiltration, no dialysis fluid is brought in contact with the dialysate side of the semipermeable membrane. Instead only a transmembrane pressure is applied over the semipermeable membrane thereby removing fluid and waste substances, from the blood through the semipermeable membrane wall and into the dialysate side thereof (convective flow). Fluid and waste substances are then passed to drain. To replace some of the removed fluid, a correctly balanced electrolyte/buffer dialysis fluid (also named infusion fluid or replacement fluid) is infused into the extracorporeal blood circuit. This infusion may be done either upstream the dialyzer (pre-infusion mode) or downstream the dialyzer (post-infusion mode) or both.

Hemodiafiltration is a combination of hemodialysis and hemofiltration, a treatment mode that combines transport of waste substances and excess fluids through the semipermeable wall by both diffusion and convection. Thus, here a dialysis fluid is brought in contact with the dialysate side of the semipermeable membrane in a continuously flowing manner, and a dialysis fluid (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible. When home dialysis is performed patients are free to perform dialysis more frequently and also in more gentle treatments with longer treatment times, i.e. 4-8 hours per treatment and 5-7 treatments per week. The dose and treatment times may be adjusted due to different demand of the patients.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patient status. Also here the removal of waste substances and excess fluid from the patient is effected by any or a combination of the treatment modes hemodialysis, hemofiltration and hemodiafiltration.

In a peritoneal dialysis treatment a hypertonic dialysis fluid is infused into the peritoneal cavity of the patient. In this treatment solutes and water is exchanged in the capillary vessels of a patient's peritoneal membrane with said hypertonic dialysis fluid. The principle of this method is diffusion of solutes transferred according to the concentration gradient and water migration due to the osmotic differences over the peritoneal membrane.

The dialysis fluids used in all the above dialysis techniques contain mainly electrolytes like sodium, magnesium, calcium, potassium, an acid/base buffer system and optionally glucose or a glucose-like compound. All the components in dialysis fluids are selected to control the levels of electrolytes and the acid-base equilibrium within the blood and to remove waste materials from the blood.

Dialysis fluids are today prepared from different types of concentrates. These may be liquid concentrates of different degree of concentration, where the acid/-electrolyte part is separated from the buffer part.

The concentrates may further be provided in highly concentrated volumes of 1-8 L in bags, or in more diluted concentrated volumes of 5-20 L in canisters. The bags may be for bedside use, for mixing within a fluid preparation unit into a ready-to-use dialysis fluid.

The concentrates may also be provided as dry concentrates for dilution into liquid concentrates and further mixing within a fluid preparation unit into a dialysis fluid.

Concentrates may also be prepared in central tanks in volumes of typically 300-1000 L.

Alternatively, the concentrates illustrated herein may be provided as liquid concentrates divided between different compartments within a multi-compartment bag. These liquid concentrates are then mixed to prepare the ready-to-use dialysis fluid. This mixing may be performed by breaking a seal between the different compartments, but it may also be performed by having the different liquid concentrates being led from the different compartments to a fluid preparation unit for mixing therein into a dialysis fluid. For example, the multicompartment bag may comprise the citrate containing concentrate in one compartment while electrolytes like calcium and magnesium are kept in a separate compartment.

As mentioned above, the dialysis fluid contains an acid for the acid/base buffer system. Historically the acid used within dialysis fluids has been acetic acid. However, in recent years citric acid has emerged as an alternative to acetic acid in dialysis fluids. While increased plasma levels of acetate may induce symptoms like general malaise, intradialytic hypotension and nausea, citrate is a natural source of energy for all cells and part of the acid-base regulation in the body. In addition, citrate is an anticoagulant and antioxidant with anti-inflammatory properties and may improve patient treatment tolerance.

However, clinical trials have shown that it is not just to replace acetic acid with citric acid. Citric acid has specific effects that need to be taken into consideration, namely its ability to form a complex with electrolytes within the dialysis fluid. This complex formation has to be compensated for when deciding on the concentrations of all the components within the dialysis fluid.

Heparin is used as an agent for anticoagulation during dialysis. Most common way of administration is by infusion of heparin, or alternatively as a bolus dose prior the start of the dialysis treatment. However, for some patients, there are drawbacks with heparin infusion like heparin induced thrombocytopenia (HIT) and increased risk of systemic bleeding in the patient.

Heparin is commonly used as anticoagulation agent in the hemodialysis methods described above but due to its drawbacks citrate has been introduced and developed as an alternative anticoagulation agent in hemodialysis.

To achieve the desired anticoagulation effect in the extracorporeal circuit a concentration of citrate in the blood of about 3 mM shall be achieved. However, today dialysis fluids comprising a concentration of citrate of only about 1 mM is commercially provided. To achieve a more complete anticoagulation, heparin must be added and act in combination with the citrate or alternatively the concentration of citrate in the dialysis composition raised. As described above, the dialysis fluid is provided as a two-, or multi-part solution before its use as dialysis solution. The two-part solution comprises an acid solution and a base solution. However, the acid solution of these two-part solutions comprises components which may form complex and precipitate in the concentrate solution. The both solutions are mixed to form a neutral and for patient compliant solution.

In WO01/21233 A1 a high citrate dialysate and uses thereof is disclosed. The application discloses a dialysate composition comprising citrate at a concentration ranging from 2.4 to 20 mEq/L (equals 0.8-6.67 mM citrate), calcium at a concentration ranging from 2.5 to 5 mEq/L (equals to 1.25-2.5 mM calcium), and magnesium at a concentration ranging from 1 to 2 mEq/L (equals 0.5-1.0 mM magnesium).

The document does not disclose an acid concentrate comprising citric acid and citrate in specific ratios.

In U.S. Pat. No. 5,252,213 it is described a dry dialysate composition comprising citrate. The dry composition may be in form of a dry mixture, pellet or tablet. The dry composition comprises an acid, a bicarbonate and a salt. The acid is preferably citric acid. After dissolving the dry composition a dialysate comprising from about 130 to about 150 mEq of Na, from 0 to about 4.0 mEq of K, from about 2.0 to 3.5 mEq Ca, from 0 to about 1.5 mEq Mg, from about 25 to about 45 mEq bicarbonate, from 0 to about 2 g glucose, and from about 90 to about 120 mEq chloride ion. The citric acid is added at a concentration from about 2 to 12 mEq, and an acid pH of the dialysate may be obtained. The components are dissolved stepwise, and by that a chemical environment is created which prevents the formation of insoluble precipitates such as calcium salts. There is no disclosure of a specific ratio of citric acid and citrate present in the dialysate.

Consequently, there is a need to increase the content of citrate in the dialysis fluid, with the purpose to replace the heparin. Also, there is a need to increase the patient compliance for those who not accept heparin.

It may seem to be an easy action to just replace the heparin by adding corresponding amount of citrate. However, this replacement has been shown to be more complicated than just a simple replacement, due to precipitations of complex formed of citrate and divalent ions like calcium ions and magnesium ions commonly present in the dialysis fluids.

By the present invention it has been shown that by thorough elaboration of parameters it has been possible to increase the concentration of citric acid and citrate in the acid concentrate dialysis solution and to avoid precipitation of undesired complex.

SUMMARY OF THE INVENTION

One object of the present invention is to provide an acid concentrate dialysis composition comprising citrate, which reduces or eliminates formation of complex between citrate and electrolytes.

An embodiment of the invention is an acid concentrate dialysis composition comprising a mixture of citric acid and citrate having pH of less than 3.0. More specifically, it is an acid concentrate dialysis composition comprising a mixture of citric acid and citrate; having pH of less than 3.0; wherein the total concentration of citrate is between 35 mM and 450 mM and the amount of citric acid is more than 50% (molar) of the total concentration of citrate. An example is an acid concentrate dialysis composition comprising a mixture of citric acid and citrate; having pH of less than 3.0; wherein the total concentration of citrate is between 35 mM and 270 mM and the amount of citric acid is more than 50% of the total concentration of citrate.

An acid concentrate having a mixture of citric acid and citrate, having a pH of less than 3.0, has shown to be less prone to precipitate.

Another embodiment is provided wherein an acid concentrate dialysis composition comprising a mixture of citric acid and citrate; having pH of less than 3.0; and wherein the amount of citric acid is more than 50% (molar) of the total concentration of citrate.

Further, the composition comprises a mixture of citric acid and citrate wherein the amount of citric acid is equal or more than 60% of the total concentration of citrate; preferably more than 70% of the total concentration, more preferably more than 75% of the total concentration, for example 80% of the total concentration of citrate. Further examples are compositions comprising a mixture of citric acid and citrate wherein the amount of citric acid is between about 70% to about 85% of the total concentrate of citrate, such as between about 75% to about 85% of the total concentrate of citrate.

Another embodiment is provided wherein the total concentration of citrate is between 35 mM and 270 mM.

In another embodiment is an acid concentrate dialysis composition provided wherein the acid concentrate dialysis composition is to be diluted and mixed with a bicarbonate-containing solution into a dialysis solution having a total concentration of citrate between 1 and 6 mM; preferably between 1 and 5 mM; more preferably between 1.0 and 4 mM, such as between 1.5 and 4 mM.

Another embodiment of the invention an acid concentrate dialysis composition as described herein, wherein the ratio of citric acid to citrate is more than 1:1. For example, the ratio of citric acid to citrate is between about 1:1 to about 10:1, preferably about 2:1 to 6:1, more preferably between about 3:1 to about 6:1.

Another embodiment of the invention is an acid concentrate dialysis composition comprising citric acid and citrate wherein total concentration of citrate is between 35 mM and 450 mM; concentration of citric acid is more than 50% or the total concentration of citrate; the ratio of citric acid to citrate is more than 1:1; and pH is less than 3.0. More specifically, an embodiment of the invention is an acid concentrate dialysis composition comprising citric acid and citrate wherein total concentration of citrate is between 35 mM and 270 mM; concentration of citric acid is more than 50% of the total concentration of citrate; the ratio of citric acid to citrate is more than 1:1; and pH is less than 3.0.

Another embodiment of the invention is an acid concentrate dialysis composition comprising citric acid and citrate wherein total concentration of citrate is between 35 mM and 450 mM; concentration of citric acid is equal or more than 60% of the total concentration of citrate; the ratio of citric acid to citrate is more than 1:1; and pH is equal or less than 2.8. More specifically, an embodiment of the invention is an acid concentrate dialysis composition comprising citric acid and citrate wherein total concentration of citrate is between 35 mM and 270 mM; concentration of citric acid is equal or more than 60% or the total concentration of citrate; the ratio of citric acid to citrate is more than 1:1; and pH is equal or less than 2.8.

More specifically, the acid concentrate dialysis composition comprises citrate in form of trisodium citrate; having a total concentration of citrate of between 35 and 450 mM; having a concentration of the citric acid equal or more than 60% of total citrate concentration; and pH is kept between 0.5 and 2.8. An example is an acid concentrate dialysis composition comprises citrate in form of trisodium citrate; having a total concentration of citrate of between 35 and 270 mM; having a concentration of the citric acid equal or more than 60% of total citrate concentration; and pH is kept between 0.5 and 2.8.

The acid concentrate dialysis solution may also comprise components and electrolytes like sodium chloride (NaCl), potassium chloride (KCl), magnesium chloride ($MgCl_2$), glucose, and calcium chloride ($CaCl_2$).

Another embodiment of the invention is the acid concentrate dialysis composition having a total concentration of citrate between 35 mM and 270 mM. Thus an acid concentrate dialysis composition comprising a mixture of citric acid and citrate; having pH of less than 3.0; and a total concentration of citrate between 35 mM and 270 mM.

A further embodiment of the invention is the composition as described above wherein the amount of citric acid in the composition is equal or more than 60% of the total concentration of citrate.

A further embodiment of the invention is a citrate containing solution comprising the acid concentrate dialysis composition as herein described, preferably in combination with physiologically acceptable electrolytes.

Another embodiment illustrated herein is a dialysis solution comprising the acid concentrate dialysis composition as herein defined. In particular a dialysis solution which may contain up to 6 mM of citrate preferably between 1.5-6.0 mM citrate. For example, the dialysis solution may comprise 1.0, 1.25, 1.5, 1.75, 2, 2.25, 2.5, 2.75, 3, 3.5, 4, 5, or 6 mM of citrate.

In one embodiment the dialysis solution comprises up to 6 mM of citrate, preferably between 1.5-6.0 mM citrate; about 130-150 mM sodium, preferably 135-145 mM sodium, or more preferably 140 mM sodium; 20-40 mM bicarbonate, preferably 25-35 mM bicarbonate, or more preferably 34 mM bicarbonate; 0-4 mM potassium; 0-1.5 mM magnesium, 0-3 mM calcium; 0-2 g/L glucose; and chloride in an amount determined by electroneutrality.

Another embodiment is a process for manufacturing an acid concentrate dialysis composition as defined herein.

Further, in another embodiment is a use of the acid concentrate dialysis composition for preparing a dialysis solution provided.

In one embodiment of the invention is a package provided containing the acid concentrate dialysis composition defined herein.

Other embodiments of the present invention are evident from the description below. All of the disclosed embodiments may not fulfill the disclosed objectives.

Definitions

The term "dialysis composition" means the composition of dialysis fluids for hemodialysis, hemodiafiltration, hemofiltration, and peritoneal dialysis, fluids for dialysis within renal intensive care, fluids for substitution or infusion normally containing buffering substances.

The term "acid concentrate of the dialysis composition" means herein the acidic part of the dialysis fluid, which is intended to be mixed with a basic composition to form the final dialysis composition, the ready-to-use dialysis fluid.

The term "citrate" means that the component is in form of a salt of citric acid, such as sodium, magnesium, calcium, or potassium salt thereof, i.e. citrate. Herein, also the citrate form of iron, selenium and zinc are included. The citric acid (denoted $C_6H_8O_7$) is deprotonated stepwise, therefore the citrate include all the different forms, citrate (denoted $C_6H_5O_7^{3-}$), hydrogen citrate (denoted $C_6H_6O_7^{2-}$), and dihydrogen citrate (denoted $C_6H_7O_7^{-}$).

The term "total concentration of citrate" means that the total amount of citric acid and any salts thereof, such as its sodium, magnesium, calcium or potassium salt thereof present in the acid concentrate of the dialysis fluid, or the dialysis fluid. However, after mixing thereof with the remaining components including the buffer, citric acid is normally converted into citrate within the fluid.

The term "electrolytes" means herein a substance that dissociate into ions in solution and acquires the capacity to conduct electricity. Sodium, potassium, calcium, magnesium, chloride are examples of electrolytes.

The term "ratio" means herein a molar ratio between the components referred to.

The term "percentage" or "%" means herein molar percentage of not otherwise specified.

DETAILED DESCRIPTION OF THE INVENTION

For patients having a chronic kidney dysfunction there is a need of improved therapies. For dialysis patients who shall avoid heparin, the selection of possible procedures of treatment is limited. A possible alternative may be a combination of treatment with heparin together with citrate. However, it would be an improved patient compliance to be able to completely replace the heparin with citrate. As stated above, when using citrate within dialysis compositions, one specific effect has to be taken into account, namely its ability to form a complex with, in particular, divalent electrolytes like calcium and magnesium and precipitate in the fluid. It is a challenge to provide dialysis solutions comprising citrate in a concentration of more than 1 mM of citrate. Most desirable is a solution having a concentration of at least 3 mM, then it would be possible to replace the heparin with citrate.

In one embodiment the acid concentrate dialysis composition of the present invention comprises a mixture of citric acid and citrate having pH of less than 3.0.

It has surprisingly been found that the acid concentrate dialysis composition comprising citric acid solution shall also comprise citrate in a specific concentration and/or ratio, and be acidic with a pH less than 3.0. There are other options available to obtain desired pH of the acid concentrate dialysis composition, for example by adding a base in an amount to provide a fluid with the specified pH. Examples of suitable bases are sodium hydroxide (NaOH) and bicarbonate, such as sodium bicarbonate.

It has been found that when an acid concentrate including citric acid and citrate, and the solution is kept at pH less than 3.0, the solution is less prone to precipitate and the formation of salt complexes (for example of calcium and magnesium) is reduced. The precipitation may be substantially reduced, or completely avoided.

The acid concentrate dialysis composition comprising citric acid and citrate may comprise the components in amounts where the amount of citric acid in the composition is more than 50% of the total concentration of citrate. For example, the amount of citric acid is equal or more than 60% of the total concentration of citrate; further example more than 70% of the total concentration, or more than 75 of the total concentration, for example 80% of the total concentration. The acid concentrate dialysis composition comprising citric acid and citrate may comprise the components in amounts where the citric acid on the composition is between 70 and 85%, such as between 75 and 85%. The acid concentrate may comprise citric acid in an amount of 70, 75, 80, or 85%.

In one embodiment of the invention is an acid concentrate dialysis composition comprising a mixture of citric acid and citrate; wherein the amount of citric acid in the composition is equal or more than 60% of the total concentration of citrate; having pH of less than 2.8.

Further, an acid concentrate dialysis solution as has been described herein comprises the citric acid and the citrate in a specified ratio. The acid concentrate dialysis composition comprises the citric acid and citrate in a balanced form, wherein the ratio of citric acid to citrate is more than 1:1, thus equal amounts of the two specified components. Another example is where the ratio of citric acid to citrate is more than 2:1.

Another example is where the ratio of citric acid to citrate is between about 1:1 to about 10:1, for example about 1:1 to about 6:1. Examples of suitable ratios are 1:1, 1.5:1, 2:1, 2.5:1, 3:1, 3.5:1, 4:1, 4.5:1, 5:1, 5.5:1, 6:1, 7:1, 8:1, 9:1, and 10:1.

It has been shown advantageously to select a specific ratio of the content of citric acid and the citrate, to avoid precipitation of calcium complex with citrate.

Another embodiment of the invention is an acid concentrate dialysis composition comprising a mixture of citric acid and citrate; wherein the ratio of citric acid to citrate is more than 1:1; having pH of less than 3.0.

Further stability of the acid concentrate dialysis composition may be achieved in compositions comprising a mixture of citrate and citric acid in a specified concentration, with a specific ratio between the citric acid and citrate, together with a determined total concentration of citrate.

In one embodiment of the invention is an acid concentrate dialysis composition comprising a mixture of citric acid and citrate; wherein the amount of citric acid in the composition is more than 50% of the total concentration of citrate; wherein the ratio of citric acid to citrate is more than 1:1; having pH of less than 3.0.

The pH of the acid concentrate dialysis composition shall be less than 3.0, to avoid the forming of calcium complex, and to obtain a more stable concentrate composition. The acid concentrate dialysis composition as described herein shall have a pH of less than 2.8, for example the pH of the concentrate composition is less than 2.6, such as less than 2.5. For example, the acid concentrate dialysis composition has a pH of between 0.5 and 2.8; preferably pH between 1.0 and 2.6; more preferably, pH between 1.5 and 2.5.

For example the pH is more than pH 1.5, and less than pH 2.6; preferably pH is between 1.5 and 2.5; more preferably pH is between 2 and 2.4, for example between 2 and 2.2.

Further, in one embodiment of the invention an acid concentrate dialysis composition is provided wherein the total concentration of citrate is up to 450 mM; the ratio of citric acid to citrate is more than 1:1; and pH is less than 3.0, preferably the total concentration of citrate is up to 270 mM.

Further, in one embodiment of the invention an acid concentrate dialysis composition is provided wherein the total concentration of citrate is up to 450 mM; the ratio of citric acid to citrate is between 1:1 and about 10:1; and pH is between 1.5 and 2.5, preferably the total concentration of citrate is up to 270 mM.

The acid concentrate dialysis composition provided may have a total concentration of citrate of between 35-270 mM; a ratio of citric acid to citrate between 2:1 and about 6:1; and pH is between 1.5 and 2.5.

In the acid concentrate dialysis composition described herein, the total concentration of citric acid and citrate may be selected between 35 mM and 270 mM.

The citrate may be present in form of sodium, potassium, calcium, or magnesium salt of citric acid. Also salts of iron, selenium and zinc are suitable for the acid concentrate dialysis composition illustrated herein. There are different salts available for the acid concentrate dialysis composition as defined herein. These are, for example, selected from sodium dihydrogen citrate, disodium hydrogen citrate, trisodium citrate, trisodiumcitrate dehydrate, potassium dihydrogen citrate, dipotassium hydrogen citrate, calcium citrate, and magnesium citrate. More specifically, the acid concentrate dialysis composition is selected from trisodium citrate, disodium hydrogencitrate, and monosodium dihydrogencitrate.

In one embodiment an acid concentrate dialysis composition comprising trisodium citrate is provided.

Another embodiment of the invention an acid concentrate dialysis composition is provided wherein the citrate is trisodium citrate; total concentration of citrate is less than 270 mM; citric acid is present in an amount of 60% of total concentration of citrate; pH is between 0.5 and 2.8.

Another embodiment of the invention an acid concentrate dialysis composition is provided wherein the citrate is trisodium citrate; total concentration of citrate is between 35 mM and 270 mM; concentration of the citric acid is equal or more than 35 mM; and pH is between 0.5 and 2.8, preferably pH is between 1.0 and 2.6; more preferably pH is between 1.5 and 2.5.

Salts of citric acid to be used in the acid concentrate dialysis composition may be formed by forming sodium, potassium, calcium, or magnesium salt, citrates. As citrate is trivalent there are different forms available for salts of citric acid. All these different forms are intended to be included in the invention presented herein. The different forms of citrates are sodium dihydrogen citrate, disodium hydrogen citrate, trisodium citrate, trisodiumcitrate di hydrate, potassium dihydrogen citrate, dipotassium hydrogen citrate, calcium citrate, and magnesium citrate.

Preferably, citrate to be included in composition described herein is selected from trisodium citrate, disodium hydrogencitrate, and monosodium dihydrogencitrate.

The acid concentrate dialysis compositions may also comprise one or more electrolytes to form a suitable dialysis solution. Components to be included together with the citric acid and the citrate are physiologically acceptable cations such as sodium ($Na^+$), potassium ($K^+$), calcium ($Ca^{2+}$), magnesium ($Mg^{2+}$), and chloride ($Cl^-$).

Dialysis solutions may also contain components like glucose. Therefore the present acid concentrate dialysis composition may contain certain amount of glucose, for example in a concentration of 0-11 mM.

The acid concentrate dialysis composition may also comprise components like physiologically acceptable buffering anions. Examples of such suitable components are acetate and lactate, or salts thereof. These components may be present in the acid concentrate dialysis composition in an amount of 0.01 to 150 mM. The dialysis fluid prepared from the acid concentrate dialysis composition may comprise the physiologically acceptable buffering anions in a concentration of 0.2 to 0.5 mM.

Thus, the acid concentrate compositions may comprise, besides the citrate and citric acid, further components like: sodium, potassium, magnesium, chloride, glucose, calcium, to form an acid concentrate composition intended to be combined and mixed with a base, for example a basic solution comprising bicarbonate to form a final dialysis composition. The solution provided is then suitable for the dialysis treatments described herein.

An example of acid concentrate dialysis composition is an acid concentrate comprising:

The compositions of the invention are acid concentrate dialysis solution intended to be diluted before use in a dialysis treatment. The concentrated compositions shall be diluted more than 30 times before its use (thus 1 part concentrate to be mixed with 29 parts water). For example, the acid concentrate dialysis composition is diluted 35 times (1:35), thus dilution according to 1+34. Another option is to dilute the acid concentrate dialysis composition 45 times (1:45), thus to dilute according to 1+44. A further option is an acid concentrate for dilution 200 times (1:200). This acid concentrate does not contain any sodium chloride. Sodium chloride is provided from a separate source when preparing the ready-to-use dialysis solution. These dilutions shall be considered as examples, not any limitation.

An acid concentrate dialysis composition may have the following general composition:

General Composition for dilution 1:35 and 1:45, respectively (amounts in mM):

|  | in diluted solution | in concentrate (1:35) | in concentrate0 (1:45) |
|---|---|---|---|
| Sodium ($Na^+$) | 95-115 | 3320-4030 | 4270-5180 |
| Potassium ($K^+$) | 0-4 | 0-140 | 0-180 |
| Calcium ($Ca^{2+}$) | 0-3 | 0-105 | 0-135 |
| Magnesium ($Mg^{2+}$) | 0-1.5 | 0-53 | 0-68 |

General Composition for dilution 1:35 and 1:45, respectively (amounts in mM):

|  | in diluted solution | in concentrate (1:35) | in concentrate0 (1:45) |
|---|---|---|---|
| Citrate | 1-6 | 35-210 | 45-270 |
| Glucose | 0-11 | 0-390 | 0-500 |

Chloride present in amount to obtain electroneutrality.

An acid concentrate dialysis composition may have the following compositions shown by Compositions I, II, III, IV, V, and VI. The concentrates presented are suitable for 1.35 and 1:45 dilution, respectively.

|  | in diluted solution | in concentrate (1:35) | in concentrate (1:45) |
|---|---|---|---|
| Composition I (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.4 | 49 | 63 |
| Magnesium ($Mg^{2+}$) | 0.5 | 18 | 23 |
| Citrate | 1.0 | 35 | 45 |
| Glucose | 5.5 | 190 | 250 |
| Composition II (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.4 | 50 | 65 |
| Magnesium ($Mg^{2+}$) | 0.5 | 18 | 23 |
| Citrate | 1.25 | 44 | 56 |
| Glucose | 5.5 | 190 | 250 |
| Composition III (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.5 | 52 | 67 |
| Magnesium ($Mg^{2+}$) | 0.5 | 18 | 23 |
| Citrate | 1.5 | 53 | 68 |
| Glucose | 5.5 | 190 | 250 |
| Composition IV (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.5 | 53 | 68 |
| Magnesium ($Mg^{2+}$) | 0.5 | 18 | 23 |
| Citrate | 1.75 | 61 | 79 |
| Glucose | 5.5 | 190 | 250 |
| Composition V (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.6 | 54 | 70 |
| Magnesium ($Mg^{2+}$) | 0.5 | 18 | 23 |
| Citrate | 2.0 | 70 | 90 |
| Glucose | 5.5 | 190 | 250 |
| Composition VI (amounts in mM): | | | |
| Sodium ($Na^+$) | 103 | 3600 | 4640 |
| Potassium ($K^+$) | 3.0 | 105 | 135 |
| Calcium ($Ca^{2+}$) | 1.6 | 52 | 72 |
| Magnesium ($Mg^{2+}$) | 0.5 | 18 | 23 |
| Citrate | 2.25 | 79 | 101 |
| Glucose | 5.5 | 190 | 250 |

Chloride present in amount to obtain electroneutrality.

The acid concentrate dialysis solution is intended to be used in hemodialysis, for example in dialysis methods like hemofiltration or hemodiafiltration.

A content of citrate and citric acid below 6 mM in a solution ready-to-use as dialysis solution is considered suitable and intended to be used for providing a complete anticoagulation effect. Preferably, the heparin usually used in hemodialysis treatments is replaced with citrate containing products.

The acid concentrate dialysis composition as herein described is intended to be mixed with a physiologically acceptable diluent.

Another embodiment of the invention is a citrate containing dialysis solution comprising the acid concentrate dialysis composition and a physiologically acceptable diluent.

The physiologically acceptable diluent is, for example, a bicarbonate containing solution.

The acid concentrate dialysis composition is to be diluted into a dialysis solution having a total concentration of citrate, thus total concentration of citrate and citric acid, being between 1 mM and 6 mM, for example, the total concentration is between 1 and 5 mM; preferably between 1.5 and 4 mM, for example between 1.5 and 3 mM. For example, the dialysis solution may comprise 1.5, 2, 2.25, 2.5, 2.75, 3, 3.5, 4, 5, or 6 mM.

Another embodiment of the invention is a citrate containing dialysis solution comprising 1 to 6 mM citrate.

The acid concentrate dialysis composition provided wherein the acid concentrate dialysis composition is to be diluted and mixed with a bicarbonate-containing solution into a dialysis solution having a total concentration of citrate between 1 and 6 mM; preferably between 1 and 5 mM; more preferably between 1.5 and 4 mM, and has a physiologically acceptable pH of between 6.5-8, more preferably pH of 6.8-7.5, for example pH of 7.0-7.4.

The acid concentrate dialysis composition is intended to be mixed with a base solution into a final dialysis fluid which may contain
up to 6 mM of citrate,
about 130-150 mM sodium, preferably 135-145 mM sodium, or more preferably 140 mM sodium;
and 20-40 mM bicarbonate, preferably 25-35 mM bicarbonate, or more preferably 34 mM bicarbonate;
0-4 mM potassium;
0-1.5 mM magnesium;
0-3 mM calcium;
0-2 g/L glucose; and
chloride determined by electroneutrality, and has a physiologically acceptable pH of between 6.5-8, more preferably pH of 6.8-7.5, for example pH of 7.0-7.4.

The dialysis fluid may comprise potassium ions in a concentration of 0-4 mM. For example the dialysis fluid comprises 0, 1, 2, 3, or 4 mM of potassium. The potassium ions may be added as potassium chloride, or any other physiologically acceptable form.

The dialysis fluid may comprise magnesium ions in a concentration of 0-1.5, for example in a concentration of 0, 0.5, 0.75, 1.0, 1.25, or of 1.5 mM. The magnesium ions may be added as magnesium chloride, or any other physiologically acceptable form.

The dialysis fluid may comprise calcium ions in a concentration of 0-3 mM, for example in a concentration of 0, 0.5, 0.75, 1, 1.25, 1.5, 1.75, 2, 2.25, 2.5, 2.75, and 3 mM. The calcium ions may be added as calcium chloride, or any other physiologically acceptable form.

When increasing the amount of total citrate within the dialysis fluid, the amount of bicarbonate has to be adjusted towards the lower end of the ranges given above. This applies especially when citrate is added to the composition.

A citrate containing dialysis solution comprising the acid concentrate dialysis composition as herein described is one of the embodiments of the invention. This dialysis solution may have a total concentration of citrate of between 1 to 6 mM.

In an embodiment illustrated is an acid concentrate dialysis composition comprising citric acid and citrate wherein total concentration of citrate is between 35 mM and 270 mM; concentration of citric acid is more than 50% or the total concentration of citrate; the ratio of citric acid to total concentration of citrate is more than 1:1; and pH is less than 3.0.

In another embodiment illustrated is an acid concentrate dialysis composition comprising citric acid and citrate wherein total concentration of citrate is between 35 mM and 270 mM; concentration of citric acid is equal or more than 60% or the total concentration of citrate; the ratio of citric acid to total concentration of citrate is more than 1:1; and pH is equal or less than 2.8.

The acid concentrate dialysis composition may be manufactured by a process comprising the following steps:
a) dissolve the sodium chloride in water
b) dissolve the electrolytes (i.e. potassium, calcium, magnesium) by mixing with the mixture of a)
c) dissolve the citric acid;
d) mix the dissolved ions of a, b and c;
e) dissolve the citrate and add the dissolved citrate to the product obtained in d)
and wherein step a), b), c), and d) are performed sequentially, in any order, or two or more steps simultaneously.

The acid concentrate dialysis composition may be provided in a package. The package may be for example a bag, or canister. The package may also be in form of a multicompartment bag, or in form of separate bags containing the above defined components. In one embodiment illustrated herein is a multicompartment bag wherein the acid concentrate dialysis composition comprising the citric acid and citrate is held in one compartment; and calcium and magnesium are kept in a separate compartment of the package. More specifically, the first compartment comprises sodium chloride, potassium chloride, glucose, citric acid, and citrate; and the second compartment comprises calcium chloride, and magnesium chloride.

EXAMPLES

By way of example, without any limitation of the scope, the following examples identify a variety of dialysis compositions pursuant to embodiments of the present invention.

Acid concentrates of the dialysis fluid contain further components in addition to the citric acid and citrate. These additional components may be sodium, potassium, magnesium, chloride, glucose. More specifically the components may be present as sodium chloride (NaCl); potassium chloride (KCl); magnesium Chloride ($MgCl_2$), glucose; calcium chloride, citric acid, and citrate, preferably in form of trisodium citrate.

For magnesium chloride and calcium chloride there are different hydrated forms available, for example $MgCl_2 \times 6H_2O$, $MgCl_2 \times 4.5H_2O$, and $MgCl_2$ anhydrous; $CaCl_2 \times 2H_2O$, and $CaCl_2$. Glucose may be present as anhydrous glucose or hydrous glucose.

In the following examples, compositions as above have been prepared. The amounts of each component as were included in the compositions are specified the following Examples.

The compositions described herein were manufactured according to the following scheme:

dissolving the sodium chloride in water;
adding citric acid, calcium chloride, and magnesium chloride; and
adding citrate to the mixture.

The amounts added of citric acid, citrate and calcium have been varied while the sodium chloride, potassium chloride, magnesium chloride, and glucose were kept constant.

Tests of pH of the compositions have then followed. The pH measurements were performed with pH meter Orion, Model 420 A.

Example 1

| Ingredient: | Diluted solution | Concentrate (1:35) |
| --- | --- | --- |
| Sodium chloride (NaCl) | 100 mM | 3500 mM |
| Potassium chloride (KCl) | 3.00 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.40 mM | 49.0 mM |
| Citric acid (anhydrous) | 1.0 mM | 35.0 mM |
| Citrate (trisodium citrate) | 0 mM | 0 mM |
| pH of the dialysis composition | | 1.6 |
| Total amount citrate | 1.0 mM | 35.0 mM |
| Content of citric acid (% of total concentration of citrate) | 100 | |

Example 2

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.44 mM | 50.3 mM |
| Citric acid (anhydrous) | 1.25 mM | 43.8 mM |
| Citrate (trisodium citrate) | 0 mM | 0 mM |
| pH of the dialysis composition | | 1.5 |
| Total amount citrate | 1.25 mM | 43.8 mM |
| Content of citric acid (% of total concentration of citrate) | 100 | |

Example 3

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.44 mM | 50.3 mM |
| Citric acid (anhydrous) | 1.00 mM | 35.0 mM |
| Citrate (trisodium citrate) | 0.25 mM | 8.75 mM |
| pH of the dialysis composition | | 2.3 |
| Total amount citrate | 1.25 mM | 43.8 mM |
| Content of citric acid (% of total concentration of citrate) | 80 | |

Example 4

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.48 mM | 51.7 mM |
| Citric acid (anhydrous) | 1.25 mM | 43.8 mM |
| Citrate (trisodium citrate) | 0.25 mM | 8.75 mM |
| pH of the dialysis composition | | 2.2 |
| Total amount citrate | 1.50 mM | 52.5 mM |
| Content of citric acid (% of total concentration of citrate) | 83 | |

Example 5

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.51 mM | 53.0 mM |
| Citric acid (anhydrous) | 1.50 mM | 52.5 mM |
| Citrate (trisodium citrate) | 0.25 mM | 8.75 mM |
| pH of the dialysis composition | | 2.1 |
| Total amount citrate | 1.75 mM | 61.3 mM |
| Content of citric acid (% of total concentration of citrate) | 86 | |

Example 6

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.55 mM | 54.3 mM |
| Citric acid (anhydrous) | 1.50 mM | 52.5 mM |
| Citrate (trisodium citrate) | 0.50 mM | 17.5 mM |
| pH of the dialysis composition | | 2.5 |
| Total amount citrate | 2.00 mM | 70.0 mM |
| Content of citric acid (% of total concentration of citrate) | 75 | |

Example 7

| Ingredient: | Diluted solution | Concentrate (1:35) |
| --- | --- | --- |
| Sodium chloride (NaCl) | 100 mM | 3500 mM |
| Potassium chloride (KCl) | 3.0 mM | 105 mM |
| Magnesium Chloride Hexahydrate($MgCl_2*6H_2O$) | 0.50 mM | 17.5 mM |
| Glucose (anhydrous) | 1.0 g/l | 35.0 g/l |
| Calciumchloride dihydrate ($CaCl_2*2H_2O$) | 1.55 mM | 54.3 mM |

-continued

| Ingredient: | Diluted solution | Concentrate (1:35) |
|---|---|---|
| Citric acid (anhydrous) | 1.60 mM | 56.0 mM |
| Citrate (trisodium citrate) | 0.40 mM | 14.0 mM |
| pH of the dialysis composition | | 2.3 |
| Total amount citrate | 2.00 mM | 70.0 mM |
| Content of citric acid (% of total concentration of citrate) | | 80 |

Example 8

| Ingredient: | Diluted solution | Concentrate (1:35) |
|---|---|---|
| Sodium chloride (NaCl) | 100 mM | 3500 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (anhydrous) | 1.0 g/l | 35.0 g/l |
| Calciumchloride dihydrate (CaCl$_2$*2H$_2$O) | 1.59 mM | 55.6 mM |
| Citric acid (anhydrous) | 1.50 mM | 52.5 mM |
| Citrate (trisodium citrate) | 0.75 mM | 26.3 mM |
| pH of the dialysis composition | | 2.8 |
| Total amount citrate | 2.25 mM | 78.8 mM |
| Content of citric acid (% of total concentration of citrate) | | 67 |

Precipitation occurred after a week

Example 9

| Ingredient: | Diluted solution | Concentrate (1:35) |
|---|---|---|
| Sodium chloride (NaCl) | 100 mM | 3500 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (anhydrous) | 1.0 g/l | 35.0 g/l |
| Calciumchloride dihydrate (CaCl$_2$*2H$_2$O) | 1.59 mM | 55.6 mM |
| Citric acid (anhydrous) | 1.75 mM | 61.3 mM |
| Citrate (trisodium citrate) | 0.50 mM | 17.0 mM |
| pH of the dialysis composition | | 2.5 |
| Total amount citrate | 2.25 mM | 78.8 mM |
| Content of citric acid (% of total concentration of citrate) | | 78 |

Example 10

| Ingredient: | Diluted solution | Concentrate (1:35) |
|---|---|---|
| Sodium chloride (NaCl) | 100 mM | 3500 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (anhydrous) | 1.0 g/l | 35.0 g/l |
| Calciumchloride dihydrate (CaCl$_2$*2H$_2$O) | 1.48 mM | 51.7 mM |
| Citric acid (anhydrous) | 1.00 mM | 35.0 mM |
| Citrate (trisodium citrate) | 0.50 mM | 17.5 mM |
| pH of the dialysis composition | | 2.8 |
| Total amount citrate | 1.50 mM | 52.5 mM |
| Content of citric acid (% of total concentration of citrate) | | 67 |

Example 11

| Ingredient: | Diluted solution | Concentrate (1:35) |
|---|---|---|
| Sodium chloride (NaCl) | 100 mM | 3500 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (anhydrous) | 1.0 g/l | 35.0 g/l |
| Calciumchloride dihydrate (CaCl$_2$*2H$_2$O) | 1.51 mM | 53.0 mM |
| Citric acid (anhydrous) | 1.25 mM | 43.8 mM |
| Citrate (trisodium citrate) | 0.50 mM | 17.5 mM |
| pH of the dialysis composition | | 2.6 |
| Total amount citrate | 1.75 mM | 61.3 mM |
| Content of citric acid (% of total concentration of citrate) | | 71 |

Example 12

| Ingredient: | Diluted solution | Concentrate (1:35) |
|---|---|---|
| Sodium chloride (NaCl) | 100 mM | 3500 mM |
| Potassium chloride (KCl) | 3.00 mM | 105 mM |
| Magnesium Chloride Hexahydrate(MgCl$_2$*6H$_2$O) | 0.50 mM | 17.5 mM |
| Glucose (anhydrous) | 1.00 g/l | 35.0 g/l |
| Calciumchloride dihydrate (CaCl$_2$*2H$_2$O) | 1.48 mM | 51.7 mM |
| Citric acid (anhydrous) | 1.25 mM | 43.8 mM |
| Citrate (trisodium citrate) | 0.25 mM | 8.75 mM |
| pH of the dialysis composition | | 2.2 |
| Total amount citrate | 1.50 mM | 52.5 mM |
| Content of citric acid (% of total concentration of citrate) | | 83 |

Example 13

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.44 mM | 64.7 mM |
| Citric acid (anhydrous) | 1.00 mM | 45.0 mM |
| Citrate (trisodium citrate) | 0.25 mM | 11.3 mM |
| pH of the dialysis composition | | 2.2 |
| Total amount citrate | 1.25 mM | 56.3 mM |
| Content of citric acid (% of total concentration of citrate) | | 80 |

Example 14

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.48 mM | 66.4 mM |

Example 15

| Ingredient: | Diluted solution | Concentrate (1:45) |
|---|---|---|
| Citric acid (anhydrous) | 1.25 mM | 56.3 mM |
| Citrate (trisodium citrate) | 0.25 mM | 11.3 mM |
| pH of the dialysis composition | | 2.1 |
| Total amount citrate | 1.50 mM | 67.5 mM |
| Content of citric acid (% of total concentration of citrate) | 83 | |

Example 15

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.51 mM | 68.1 mM |
| Citric acid (anhydrous) | 1.5 mM | 67.5 mM |
| Citrate (trisodium citrate) | 0.25 mM | 11.3 mM |
| pH of the dialysis composition | | 2.0 |
| Total amount citrate | 1.75 mM | 78.8 mM |
| Content of citric acid (% of total concentration of citrate) | 86 | |

Example 16

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.55 mM | 69.8 mM |
| Citric acid (anhydrous) | 1.50 mM | 67.5 mM |
| Citrate (trisodium citrate) | 0.50 mM | 22.5 mM |
| pH of the dialysis composition | | 2.4 |
| Total amount citrate | 2.00 mM | 90.0 mM |
| Content of citric acid (% of total concentration of citrate) | 75 | |

Example 17

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 64.7 mM |
| Citric acid (anhydrous) | 1.00 mM | 45.0 mM |
| Citrate (trisodium citrate) | 0.75 mM | 33.8 mM |
| pH of the dialysis composition | | 3.0 |
| Total amount citrate | 1.75 mM | 78.8 mM |
| Content of citric acid (% of total concentration of citrate) | 57 | |

The solution was stored at room temperature. Precipitation observed after 1 day.

Example 18

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.25 mM | 56.3 mM |
| Citrate (trisodium citrate) | 0.75 mM | 33.8 mM |
| pH of the dialysis composition | | 2.8 |
| Total amount citrate | 2.00 mM | 90.0 mM |
| Content of citric acid (% of total concentration of citrate) | 63 | |

The solution was stored at room temperature. Precipitation observed after 4 days.

Example 19

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.00 mM | 45.0 mM |
| Citrate (trisodium citrate) | 0.50 mM | 22.5 mM |
| pH of the dialysis composition | | 2.7 |
| Total amount citrate | 1.50 mM | 67.5 mM |
| Content of citric acid (% of total concentration of citrate) | 67 | |

The solution was stored at 40 degrees Celsius. Precipitation observed after 4 days.

Example 20

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.00 mM | 45.0 mM |
| Citrate (trisodium citrate) | 0.75 mM | 33.8 mM |
| pH of the dialysis composition | | 3.0 |
| Total amount citrate | 1.75 mM | 78.8 mM |
| Content of citric acid (% of total concentration of citrate) | 57 | |

Precipitation observed directly after preparation.

Example 21

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride | 0.50 mM | 22.5 mM |

19
-continued

| Ingredient: | Diluted solution | Concentrate (1:45) |
|---|---|---|
| Hexahydrate(MgCl$_2$*6H$_2$O) | | |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.25 mM | 56.3 mM |
| Citrate (trisodium citrate) | 0.50 mM | 22.5 mM |
| pH of the dialysis composition | | 2.5 |
| Total amount citrate | 1.75 mM | 67.5 mM |
| Content of citric acid (% of total concentration of citrate) | 71 | |

The solution was stored at 40 degrees Celsius. Precipitation observed after 4 days.

Example 22

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.25 mM | 56.3 mM |
| Citrate (trisodium citrate) | 0.75 mM | 33.8 mM |
| pH of the dialysis composition | | 2.8 |
| Total amount citrate | 2.00 mM | 90.0 mM |
| Content of citric acid (% of total concentration of citrate) | 63 | |

Precipitation observed directly after preparation of solution.

Example 23

| Ingredient: | Diluted solution | Concentrate (1:45) |
|---|---|---|
| Sodium chloride (NaCl) | 100 mM | 4500 Mm |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.25 mM | 56.3 mM |
| Citric acid (anhydrous) | 1.50 mM | 67.5 mM |
| Citrate (trisodium citrate) | 0.50 mM | 22.5 mM |
| pH of the dialysis composition | | 2.2 |
| Total amount citrate | 2.00 mM | 90.0 mM |
| Content of citric acid (% of total concentration of citrate) | 75 | |

The solution was stored at 40 degrees Celsius. Precipitation observed after after 4.5 months. Contamination of sample is not excluded.

Example 24

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.4 mM | 63 mM |
| Citric acid (anhydrous) | 1.0 mM | 45 mM |
| Citrate (trisodium citrate) | 0 mM | 0 mM |

20
-continued

| Ingredient: | Diluted solution | Concentrate (1:45) |
|---|---|---|
| pH of the dialysis composition | | 1.29 |
| Total amount citrate | 1.0 mM | 45.0 mM |
| Content of citric acid (% of total concentration of citrate) | 100 | |

Example 25

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.44 mM | 64.7 mM |
| Citric acid (anhydrous) | 1 mM | 45.0 mM |
| Citrate (trisodium citrate) | 0.25 mM | 11.3 mM |
| pH of the dialysis composition | | 2.21 |
| Total amount citrate | 1.25 mM | 66.3 mM |
| Content of citric acid (% of total concentration of citrate) | 80 | |

Example 26

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.48 mM | 66.4 mM |
| Citric acid (anhydrous) | 1.25 mM | 56.3 mM |
| Citrate (trisodium citrate) | 0.25 mM | 11.2 mM |
| pH of the dialysis composition | | 2.07 |
| Total amount citrate | 1.50 mM | 67.5 mM |
| Content of citric acid (% of total concentration of citrate) | 83 | |

Example 27

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.51 mM | 68.1 mM |
| Citric acid (anhydrous) | 1.50 mM | 67.5 mM |
| Citrate (trisodium citrate) | 0.25 mM | 11.2 mM |
| pH of the dialysis composition | | 1.96 |
| Total amount citrate | 1.75 mM | 78.7 mM |
| Content of citric acid (% of total concentration of citrate) | 86 | |

Example 28

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.55 mM | 69.8 mM |
| Citric acid (anhydrous) | 1.50 mM | 67.5 mM |
| Citrate (trisodium citrate) | 0.50 mM | 22.5 mM |
| pH of the dialysis composition | | 2.24 |
| Total amount citrate | 2.00 mM | 90.0 mM |
| Content of citric acid (% of total concentration of citrate) | | 75 |

Example 29

| Ingredient: | Diluted solution | Concentrate (1:45) |
|---|---|---|
| Sodium chloride (NaCl) | 102 mM | 4604 mM |
| Potassium chloride (KCl) | 4.0 mM | 180 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.75 mM | 78.8 mM |
| Citric acid (anhydrous) | 0.75 mM | 33.8 mM |
| Citrate (trisodium citrate) | 0.25 mM | 11.2 mM |
| pH of the dialysis composition | | 2.37 |
| Total amount citrate | 1.0 mM | 45.0 mM |
| Content of citric acid (% of total concentration of citrate) | | 75 |

Example 30

| Ingredient: | Diluted solution | Concentrate (1:45) |
|---|---|---|
| Sodium chloride (NaCl) | 102 mM | 4608 mM |
| Potassium chloride (KCl) | 4.0 mM | 180 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.75 mM | 78.8 mM |
| Citric acid (anhydrous) | 0.80 mM | 36.0 mM |
| Citrate (trisodium citrate) | 0.20 mM | 9.0 mM |
| pH of the dialysis composition | | 2.18 |
| Total amount citrate | 1.0 mM | 45.0 mM |
| Content of citric acid (% of total concentration of citrate) | | 80 |

Example 31

| Ingredient: | Diluted solution | Concentrate (1:45) |
|---|---|---|
| Sodium chloride (NaCl) | 103 mM | 4615 mM |
| Potassium chloride (KCl) | 4.0 mM | 180 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.75 mM | 78.8 mM |
| Citric acid (anhydrous) | 0.85 mM | 38.2 mM |
| Citrate (trisodium citrate) | 0.15 mM | 6.8 mM |
| pH of the dialysis composition | | 2.06 |
| Total amount citrate | 1.0 mM | 45.0 mM |
| Content of citric acid (% of total concentration of citrate) | | 85 |

Example 32

| Ingredient: | Diluted solution | Concentrate (1:45) |
|---|---|---|
| Sodium chloride (NaCl) | 103 mM | 4622 mM |
| Potassium chloride (KCl) | 4.0 mM | 180 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.75 mM | 78.8 mM |
| Citric acid (anhydrous) | 0.90 mM | 40.5 mM |
| Citrate (trisodium citrate) | 0.10 mM | 4.5 mM |
| pH of the dialysis composition | | 1.77 |
| Total amount citrate | 1.0 mM | 45.0 mM |
| Content of citric acid (% of total concentration of citrate) | | 90 |

Example 33

| Ingredient: | Diluted solution | Concentrate (1:35) |
|---|---|---|
| Sodium chloride (NaCl) | 102 mM | 3584 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.40 mM | 49.0 mM |
| Citric acid (monohydrate) | 0.80 mM | 35.0 mM |
| Citrate (trisodium citrate) | 0.20 mM | 0 mM |
| pH of the dialysis composition | | 2.4 |
| Total amount citrate | 1.00 mM | 35.0 mM |
| Content of citric acid (% of total concentration of citrate) | | 80 |

Example 34

| Ingredient: | Diluted solution | Concentrate (1:35) |
|---|---|---|
| Sodium chloride (NaCl) | 102 mM | 3580 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.44 mM | 50.3 mM |
| Citric acid (monohydrate) | 1.00 mM | 35 mM |
| Citrate (trisodium citrate) | 0.25 mM | 8.8 mM |
| pH of the dialysis composition | | 2.4 |
| Total amount citrate | 1.25 mM | 43.8 mM |
| Content of citric acid (% of total concentration of citrate) | | 80 |

Example 35

| Ingredient: | Diluted solution | Concentrate (1:35) |
|---|---|---|
| Sodium chloride (NaCl) | 102 mM | 3570 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.48 mM | 51.6 mM |
| Citric acid (monohydrate) | 1.20 mM | 42 mM |
| Citrate (trisodium citrate) | 0.30 mM | 10.5 mM |
| pH of the dialysis composition | | 2.3 |
| Total amount citrate | 1.50 mM | 52.5 mM |
| Content of citric acid (% of total concentration of citrate) | 80 | |

Example 36

| Ingredient: | Diluted solution | Concentrate (1:35) |
|---|---|---|
| Sodium chloride (NaCl) | 102 mM | 3570 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.51 mM | 52.9 mM |
| Citric acid (monohydrate) | 1.40 mM | 49 mM |
| Citrate (trisodium citrate) | 0.35 mM | 12.3 mM |
| pH of the dialysis composition | | 2.3 |
| Total amount citrate | 1.75 mM | 61.3 mM |
| Content of citric acid (% of total concentration of citrate) | 80 | |

Example 37

| Ingredient: | Diluted solution | Concentrate (1:35) |
|---|---|---|
| Sodium chloride (NaCl) | 102 mM | 3560 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.55 mM | 54.3 mM |
| Citric acid (monohydrate) | 1.60 mM | 56.0 mM |
| Citrate (trisodium citrate) | 0.40 mM | 14.0 mM |
| pH of the dialysis composition | | 2.5 |
| Total amount citrate | 2.00 mM | 70.0 mM |
| Content of citric acid (% of total concentration of citrate) | 80 | |

Example 38

| Ingredient: | Diluted solution | Concentrate (1:35) |
|---|---|---|
| Sodium chloride (NaCl) | 102 mM | 3550 mM |
| Potassium chloride (KCl) | 3.0 mM | 105 mM |
| Magnesium Chloride Hexahydrate(MgCl$_2$*6H$_2$O) | 0.50 mM | 17.5 mM |
| Glucose (monohydrate) | 1.1 g/l | 38.5 g/l |
| Calciumchloride dihydrate (CaCl$_2$*2H$_2$O) | 1.59 mM | 55.6 mM |
| Citric acid (monohydrate) | 1.75 mM | 61.3 mM |
| Citrate (trisodium citrate) | 0.50 mM | 17.5 mM |
| pH of the dialysis composition | | 2.4 |
| Total amount citrate | 2.25 mM | 78.8 mM |
| Content of citric acid (% of total concentration of citrate) | 78 | |

Example 39

| Ingredient: | Diluted solution | Concentrate (1:45) |
|---|---|---|
| Sodium chloride (NaCl) | 102 mM | 4610 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.40 mM | 63.0 mM |
| Citric acid (anhydrous) | 0.80 mM | 36.0 mM |
| Citrate (trisodium citrate) | 0.20 mM | 9 mM |
| pH of the dialysis composition | | 2.23 |
| Total amount citrate | 1.00 mM | 45.0 mM |
| Content of citric acid (% of total concentration of citrate) | 80 | |

Example 40

| Ingredient: | Diluted solution | Concentrate (1:45) |
|---|---|---|
| Sodium chloride (NaCl) | 102 mM | 4600 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45.0 g/l |
| Calciumchloride dihydrate (CaCl$_2$*2H$_2$O) | 1.44 mM | 64.8 mM |
| Citric acid (anhydrous) | 1.00 mM | 45 mM |
| Citrate (trisodium citrate) | 0.25 mM | 11.2 mM |
| pH of the dialysis composition | | 2.22 |
| Total amount citrate | 1.25 mM | 56.2 mM |
| Content of citric acid (% of total concentration of citrate) | 80 | |

Example 41

| Ingredient: | Diluted solution | Concentrate (1:45) |
|---|---|---|
| Sodium chloride (NaCl) | 102 mM | 4590 mM |
| Potassium chloride (KCl) | 3.0 mM | 135 mM |
| Magnesium Chloride Hexahydrate(MgCl$_2$*6H$_2$O) | 0.50 mM | 22.5 mM |
| Glucose (anhydrous) | 1.0 g/l | 45 g/l |
| Calciumchloride dihydrate (CaCl$_2$*2H$_2$O) | 1.48 mM | 66.6 mM |
| Citric acid (anhydrous) | 1.20 mM | 54 mM |
| Citrate (trisodium citrate) | 0.30 mM | 13.5 mM |
| pH of the dialysis composition | | 2.23 |
| Total amount citrate | 1.50 mM | 67.5 mM |
| Content of citric acid (% of total concentration of citrate) | 80 | |

Example 42

| Ingredient: | Diluted solution | Concentrate (1:45) |
|---|---|---|
| Sodium chloride (NaCl) | 102 mM | 4590 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 1.51 mM | 67.95 mM |
| Citric acid (anhydrous) | 1.40 mM | 63.0 mM |
| Citrate (trisodium citrate) | 0.35 mM | 15.8 mM |
| pH of the dialysis composition | | 2.22 |
| Total amount citrate | 1.75 mM | 78.8 mM |
| Content of citric acid (% of total concentration of citrate) | 80 | |

Example 43

| Ingredient: | Diluted solution | Concentrate (1:45) |
|---|---|---|
| Sodium chloride (NaCl) | 102 mM | 4580 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 1.55 mM | 69.8 mM |
| Citric acid (anhydrous) | 1.60 mM | 72.0 mM |
| Citrate (trisodium citrate) | 0.40 mM | 18.0 mM |
| pH of the dialysis composition | | 2.21 |
| Total amount citrate | 2.00 mM | 90.0 mM |
| Content of citric acid (% of total concentration of citrate) | 80 | |

Example 44

| Ingredient: | Diluted solution | Concentrate (1:45) |
|---|---|---|
| Sodium chloride (NaCl) | 101 mM | 4570 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 1.70 mM | 76.5 mM |
| Citric acid (anhydrous) | 2.4 mM | 108 mM |
| Citrate (trisodium citrate) | 0.6 mM | 27 mM |
| pH of the dialysis composition | | 2.2 |
| Total amount citrate | 3.0 mM | 135 mM |
| Content of citric acid (% of total concentration of citrate) | 80 | |

Example 45

| Ingredient: | Diluted solution | Concentrate (1:45) |
|---|---|---|
| Sodium chloride (NaCl) | 101 mM | 4550 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 1.70 mM | 76.5 mM |
| Citric acid (anhydrous) | 2.4 mM | 108 mM |
| Citrate (trisodium citrate) | 0.60 mM | 27 mM |
| pH of the dialysis composition | | 2.2 |
| Total amount citrate | 3.0 mM | 135 mM |
| Content of citric acid (% of total concentration of citrate) | 80 | |

Example 46

| Ingredient: | Diluted solution | Concentrate (1:45) |
|---|---|---|
| Sodium chloride (NaCl) | 101 mM | 4530 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 1.85 mM | 83.2 mM |
| Citric acid (anhydrous) | 3.2 mM | 144 mM |
| Citrate (trisodium citrate) | 0.80 mM | 36 mM |
| pH of the dialysis composition | | 2.1 |
| Total amount citrate | 4.0 mM | 108 mM |
| Content of citric acid (% of total concentration of citrate) | 80 | |

Example 47

| Ingredient: | Diluted solution | Concentrate (1:45) |
|---|---|---|
| Sodium chloride (NaCl) | 100 mM | 4500 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 2.00 mM | 90.0 mM |
| Citric acid (anhydrous) | 4.0 mM | 180 mM |
| Citrate (trisodium citrate) | 1.0 mM | 45 mM |
| pH of the dialysis composition | | 2.2 |
| Total amount citrate | 5.0 mM | 225 mM |
| Content of citric acid (% of total concentration of citrate) | 80 | |

Example 48

| Ingredient: | Diluted solution | Concentrate (1:45) |
|---|---|---|
| Sodium chloride (NaCl) | 99.4 mM | 4470 mM |
| Potassium chloride (KCl) | 3.0 mM | 135 mM |
| Magnesium Chloride Hexahydrate($MgCl_2*6H_2O$) | 0.50 mM | 22.5 mM |
| Glucose (anhydrous) | 1.0 g/l | 45.0 g/l |
| Calciumchloride dihydrate ($CaCl_2*2H_2O$) | 2.15 mM | 96.75 mM |
| Citric acid (anhydrous) | 4.8 mM | 216 mM |
| Citrate (trisodium citrate) | 1.2 mM | 54 mM |
| pH of the dialysis composition | | 2.1 |
| Total amount citrate | 6.0 mM | 270 mM |
| Content of citric acid (% of total concentration of citrate) | 80 | |

Example 49

| Ingredient: | Diluted solution | Concentrate (1:200) |
|---|---|---|
| Potassium chloride (KCl) | 3.0 mM | 600 mM |
| Magnesium Chloride Hexahydrate(MgCl$_2$*6H$_2$O) | 0.50 mM | 100 mM |
| Glucose (anhydrous) | 1.0 g/l | 200 g/l |
| Calciumchloride dihydrate (CaCl$_2$*2H$_2$O) | 1.51 mM | 303 mM |
| Citric acid (anhydrous) | 1.5 mM | 300 mM |
| Citrate (trisodium citrate) | 0.25 mM | 50 mM |
| pH of the dialysis composition | | 2.1 |
| Total amount citrate | 1.75 mM | 350 mM |
| Content of citric acid (% of total concentration of citrate) | | 86 |

Example 50

| Ingredient: | Diluted solution | Concentrate (1:200) |
|---|---|---|
| Potassium chloride (KCl) | 3.0 mM | 600 mM |
| Magnesium Chloride Hexahydrate(MgCl$_2$*6H$_2$O) | 0.50 mM | 100 mM |
| Glucose (anhydrous) | 1.0 g/l | 200 g/l |
| Calciumchloride dihydrate (CaCl$_2$*2H$_2$O) | 1.55 mM | 310 mM |
| Citric acid (anhydrous) | 1.6 mM | 320 mM |
| Citrate (trisodium citrate) | 0.4 mM | 80 mM |
| pH of the dialysis composition (calculated) | | 2.2 |
| Total amount citrate | 2.0 mM | 400 mM |
| Content of citric acid (% of total concentration of citrate) | | 80 |

Solutions prepared according to Examples 1 to 12 are intended for dilution 1×35. They were stored in 40±2 degrees Celsius, and 30±2 degrees Celsius, respectively. Precipitation was observed in Example 8.

The solutions prepared according to Examples 13 to 16 were intended for dilution according to 1×45. The concentrated solutions were stored at 40±2 degrees Celsius, and 30±2 degrees Celsius, respectively during one month. No precipitation was observed.

Examples 17 to 23 were prepared for dilution according to 1×45. The concentrated solutions were stored at room temperature and 40±2 degrees Celsius, respectively. Precipitation was observed in these examples.

The solutions according to Examples 24 to 28 were intended for dilution according to 1×45. The concentrated solutions were stored at 30±2 degrees Celsius, and at 40±2 degrees Celsius, respectively during two months. No precipitation was observed.

Also the concentrates according to Examples 29 to 32 are intended for dilution 1×45.

Acid concentrates for dilution 1×35 were prepared according to Examples 33 to 38. Of those, acid concentrates according to Examples 33, 36 and 38 were stored under accelerated ageing conditions at 40±2° C. in an atmosphere with 75±5% RH. No precipitations were found.

Acid concentrates for dilution 1×45 were prepared according to Examples 39 to 48.

An acid concentrate for dilution 1×200 was prepared according to Example 49.

The acid concentrate 49 was stored at 30±2° C. during 30 days. No precipitation was found.

If not otherwise specified, the acid concentrates above stored at 30 degrees Celsius were kept in an atmosphere with 65±5% RH, while the acid concentrates stored at 40 degrees Celsius were kept in an atmosphere with 40±5% RH.

Test of pH Stability pH measurement were performed of concentrated solutions according to Examples 1-6 and 8-9. The results are presented in Table 1. The solutions according to Examples 1-6 and 8-9 were stored in glass bottles in a temperature of 40 degrees Celsius. The pH values of the solutions were measured during a time period of four weeks.

TABLE 1

| Solution according to: | pH at day 0 | pH after 1 week storage | pH after 2 weeks storage | pH after 3 weeks storage | pH after 4 weeks storage |
|---|---|---|---|---|---|
| Example 1 | 1.55 | 1.55 | 1.57 | | 1.55 |
| Example 2 | 1.50 | 1.50 | 1.59 | 1.49 | 1.5 |
| Example 3 | 2.33 | 2.33 | 2.38 | 2.32 | 2.38 |
| Example 4 | 2.22 | 2.23 | 2.21 | 2.21 | 2.28 |
| Example 5 | 2.12 | 2.15 | 2.12 | 2.11 | 2.17 |
| Example 6 | 2.53 | 2.55 | 2.54 | 2.53 | 2.59 |
| Example 8 | 2.82 | 2.83 precipitation | Finished | Finished | Finished |
| Example 9 | 2.50 | 2.40 | | | |

The acid concentrate dialysis compositions are intended to be diluted to suitable concentration. For example, the concentrated acid dialysis compositions are diluted according to 1 part dialysis composition+34 parts water (total 35 parts) water ("1×35"), alternatively 1 part with 44 parts water "1×45").

The water is of quality suitable for dialysis, either available as tap water or purified in water cleaning systems into water having quality suitable for dialysis.

The acid dialysis compositions were mixed with a base composition comprising bicarbonate (sodium bicarbonate, NaHCO$_3$).

However, all these dialysis fluids, both acetate and citrate containing dialysis fluids, further contain about 130-150 mM sodium, 135-145 mM sodium or 140 mM sodium, and 20-40 mM bicarbonate, 25-35 mM bicarbonate or 34 mM bicarbonate, and chloride determined by electro-neutrality.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An acid concentrate dialysis composition comprising:
   3500-4622 mM sodium chloride;
   105-180 mM potassium chloride;
   greater than 56.3 and up to 96.75 mM calcium chloride;
   17.5-22.5 mM magnesium chloride;
   35-45 g/L glucose;
   chloride determined by electroneutrality; and
   a mixture of citric acid and citrate, wherein the total concentration of citrate is 35 mM to 270 mM, the amount of citric acid is about 75% or more of the total concentration of citrate, and the acid concentrate dialysis composition has a pH of less than 3.0.

2. The acid concentrate dialysis composition according to claim 1, wherein the amount of citric acid is about 80% or more of the total concentration of citrate.

3. The acid concentrate dialysis composition according to claim 1, wherein the dialysis composition has a pH of less than 2.8.

4. The acid concentrate dialysis composition according to claim 1, wherein the citrate is selected from sodium, potassium, calcium, or magnesium salt of citric acid.

5. The acid concentrate dialysis composition according to claim 1, wherein the citrate is selected from sodium dihydrogen citrate, disodium hydrogen citrate, trisodium citrate, trisodiumcitrate dihydrate, potassium dihydrogen citrate, dipotassium hydrogen citrate, calcium citrate, and magnesium citrate.

6. The acid concentrate dialysis composition according to claim 1, wherein the dialysis composition has a pH of less than 2.6.

7. The acid concentrate dialysis composition according to claim 1, wherein the dialysis composition has a pH of less than 2.5.

8. The acid concentrate dialysis composition according to claim 1, wherein the citrate is selected from trisodium citrate, disodium hydrogen citrate, and monosodium dihydrogencitrate.

9. A package comprising the acid concentrate dialysis composition of claim 1.

10. A process for manufacturing the acid concentrate dialysis composition of claim 1, the process comprising:
    a) dissolving sodium chloride in water;
    b) dissolving electrolytes by mixing with the mixture of a);
    c) dissolving citric acid;
    d) mixing the sodium chloride, electrolytes, and citric acid as of a, b and c to obtain a mixture; and
    e) adding citrate to the mixture obtained in d) to obtain the acid concentrate dialysis composition, wherein step a), b), c), and d) are performed sequentially, in any order, or two or more steps simultaneously.

11. A method of preparing a dialysis solution, the method comprising:
    providing the acid concentrate dialysis composition of claim 1; and
    mixing the acid concentrate dialysis composition with a bicarbonate-containing solution.

* * * * *